United States Patent [19]

Mount et al.

[11] 4,412,940

[45] Nov. 1, 1983

[54] METHOD FOR PREPARING MALEIC ANHYDRIDE CATALYST

[75] Inventors: Ramon A. Mount; Harold Raffelson, both of St. Louis, Mo.

[73] Assignee: Monsanto Company, St. Louis, Mo.

[21] Appl. No.: 217,731

[22] Filed: Dec. 18, 1980

[51] Int. Cl.[3] .............................................. B01J 27/14

[52] U.S. Cl. .................................................... 502/209

[58] Field of Search ................................ 252/435, 437

[56] References Cited

U.S. PATENT DOCUMENTS

| | | | |
|---|---|---|---|
| 3,293,268 | 12/1966 | Bergman et al. | 260/346.8 |
| 3,915,892 | 10/1975 | Harrison | 252/435 |
| 3,985,775 | 10/1976 | Harrison | 252/437 X |
| 4,043,943 | 8/1977 | Schneider | 252/435 X |
| 4,062,873 | 12/1977 | Harrison | 252/437 X |
| 4,080,312 | 3/1978 | Farha et al. | 252/435 X |
| 4,092,269 | 5/1978 | Mount et al. | 252/437 X |
| 4,147,661 | 4/1979 | Higgins et al. | 252/435 |
| 4,209,423 | 6/1980 | Hutchings et al. | 252/435 |
| 4,244,879 | 1/1981 | Bremer et al. | 252/437 X |
| 4,283,307 | 8/1981 | Barone et al. | 252/437 X |
| 4,294,722 | 10/1981 | Bremer et al. | 252/437 X |
| 4,328,120 | 5/1982 | Udovich | 252/435 |
| 4,328,126 | 5/1982 | Udovich et al. | 252/435 |

*Primary Examiner*—Delbert E. Gantz
*Assistant Examiner*—William G. Wright
*Attorney, Agent, or Firm*—Wendell W. Brooks; Thomas N. Wallin; Thomas Y. Awalt, Jr.

[57] ABSTRACT

An improvement in a method of preparing catalysts for the manufacture of maleic anhydride by oxidizing a saturated hydrocarbon. The catalyst is prepared by a process in which a catalyst precursor, containing tetravalent vanadium, is formed into agglomerates and calcined, the improvement being calcining the catalyst precursor at 325°–375° C. in the presence of oxygen and a saturated aliphatic hydrocarbon.

5 Claims, No Drawings

METHOD FOR PREPARING MALEIC ANHYDRIDE CATALYST

BACKGROUND OF THE INVENTION

This invention relates to a method for preparing catalysts useful in the manufacture of dicarboxylic acid anhydrides by the oxidation of hydrocarbons. More particularly, it is directed to the preparation of high yield catalysts suitable for producing maleic anhydride from saturated hydrocarbons at lower temperature than heretofore thought possible.

Maleic anhydride is used alone or in combination with other acids in the manufacture of alkyd and polyester resins. It is also a versatile intermediate for chemical synthesis. Significant quantities of maleic anhydride are produced each year to satisfy these needs.

U.S. Pat. No. 3,293,268 teaches a process of oxidizing saturated aliphatic hydrocarbons to maleic anhydride under controlled temperature conditions and in the presence of phosphorus-vanadium-oxygen catalysts. A method of preparing such catalysts involved reacting phosphoric acid with a vanadium compound in aqueous hydrochloric acid solution, recovering the remaining solids by evaporating the solution to dryness, and then heating the solids to 300° to 500° C. The resulting catalysts were ground to pass a 20 mesh screen and pelleted to form tablets.

U.S. Pat. No. 3,915,892 teaches a three phase transition in which a mixed oxide of vanadium and pentavalent phosphorus in substantially the dihydrate form is subjected to:

(1) a first heat step at 370–394° C. for about 0.5–2 hours wherein the dihydrate is converted to a monohydrate;
(2) a second heat treatment at 395–425° C. wherein the monohydrate is converted to the anhydrous oxide;
(3) a third heat step for post dehydration bulk crystal phase transition at 450–520° C. at from about 4–16 hours.

In the third phase, a mixture of air and butane is used.

One of the disadvantages of this process is that it contemplates temperatures above which are most desirable in the conversion of a hydrocarbon such as butane to maleic anhydride, and therefore makes it difficult if not impossible to perform the last treatment phase in most maleic anhydride converters which are not made to withstand such temperatures. A solution to this problem, and any method for the preparation of the catalyst which increases its yield would be a significant advance in the art and are objects of this invention.

SUMMARY OF THE INVENTION

These and other objects are achieved by the process improvement disclosed for preparing catalyst comprising phosphorus, vanadium and oxygen, the phosphorus to vanadium ratio being in the range of about 1:2 to about 2:1, and wherein a substantial amount of the vanadium is in the tetravalent state.

The process comprises (a) contacting vanadium and phosphorus compounds under conditions which will provide a catalyst precursor wherein greater than 50 atom percent of the vanadium is tetravalent vanadium; (b) recovering the catalyst precursor; (c) forming the catalyst precursor into structures; and (d) calcining the catalyst precursors.

The improvement comprises calcining the catalyst precursor at 325°–375° C. in the presence of oxygen and a saturated aliphatic hydrocarbon.

For the purposes of this invention, the term "catalytic activity" means the ability to convert a particular feed stock, such as butane, at a particular temperature to other compounds. The term "selectivity" means the ratio of the moles of maleic anhydride obtained to the moles of hydrocarbon reacted. The term "yield" means the ratio of the moles of maleic anhydride obtained to the moles of feed introduced into the reaction. The term "space velocity" means the hourly volume of gaseous feed expressed in cubic centimeters (cc) at 60° F. and standard atmospheric pressure, divided by the catalyst bulk volume expressed in cubic centimeters (cc), the term expressed as cc/cc/hour.

The catalysts of this invention are particularly useful for the conversion of butane to maleic anhydride.

PREPARATION OF THE CATALYSTS

Broadly described, the catalysts of this invention are prepared by contacting vanadium and phosphorus compounds under conditions which will provide a substantial amount of vanadium in the tetravalent state to form a catalyst precursor, recovering the catalyst precursor, forming the catalyst precursor into structures for use in a maleic anhydride reactor, and calcining the structured catalyst precursor to form the catalysts.

The vanadium compounds useful as a source of vanadium in the catalyst precursors are those known to the art. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium-containing acids such as metavanadic acid, pyrovanadic acid and the like; vanadium salts such as ammonium metavanadate, vanadium sulfate, vanadium phosphate, vanadyl formate, vanadyl oxalate and the like. However, vanadium pentoxide is preferred.

As a source of phosphorus in the catalyst precursors useful phosphorus compounds are also those known to the art. Suitable phosphorus compounds include: phosphoric acids, such as metaphosphoric acid, orthophosphoric acid, triphosphoric acid, pyrophosphoric acid, phosphorous acid and the like; phosphorus oxides such as phosphorus pentoxide and the like; phosphorus halides such as phosphorus oxyiodide, phosphorus pentachloride, phosphorus oxybromide and the like; and organophosphorus compounds such as ethyl phosphate, methyl phosphate and the like. However, phosphoric acids, such as orthophosphoric acid, and phosphorous acid are preferred.

To prepare the catalyst precursors, a vanadium compound is heated with a phosphorus compound in an acid solution to dissolve the starting materials. A reducing agent is used to reduce any pentavalent vanadium to tetravalent vanadium and to maintain vanadium in the tetravalent state. As is well known to those skilled in the art, hydrogen halide acid, phosphorous or phosphoric acid solutions, which are mild reducing agents, can serve not only as the acid but also as the reducing agent for the pentavalent vanadium. The acid solution-containing phosphorus compound and vanadium compound are heated until a blue solution is obtained, indicating that a substantial amount, i.e. greater than 50 atom percent, of the vanadium is in the tetravalent state.

The amount of time required to dissolve the phosphorus and vanadium compounds and to reduce a substantial amount of the vanadium to the tetravalent state to form the catalyst precursors varies from batch to batch, depending upon the compounds used as starting materials and the temperature at which the compounds are heated. However, the solution can be analyzed to insure that most of the vanadium is in the tetravalent state.

Although any number of phosphorus compounds and vanadium compounds can be used to form the phosphorus-vanadium-oxygen precursor, the atom ratio of phosphorus to vanadium in the precursor is important since it controls the phosphorus-to-vanadium atom ratio in the final catalyst. When phosphorus-vanadium-oxygen precursors contain a phosphorus-to-vanadium atom ratio below about 1:2 or above about 2:1, the yield of maleic anhydride using the catalysts of this invention is so low that it is not of commercial significance. It is preferred that phosphorus-vanadium-oxygen precursors have a phosphorus to vanadium atom ratio in the range of about 1:1 to about 1.5:1, and more preferably a phosphorus to vanadium atom ratio of about 1:1 to about 1.2:1, say about 1.1:1.

After the vanadium and phosphorus compounds are mixed and substantially all the vanadium has been reduced to the tetravalent state, it is necessary to remove most of the water in order to recover the phosphorus-vanadium-oxygen precursors. Techniques for recovering the phosphorus-vanadium-oxygen precursors from solution are well known to those skilled in the art. The precursors can be deposited on a carrier, such as alumina or titania, from the aqueous solution, or the precursors can be dried by gentle heating to recover the solid phosphorus-vanadium-oxygen precursors from solution.

After the phosphorus-vanadium-oxygen precursors are recovered from solution, they are then formed into structures suitable for use in a maleic anhydride reactor. Techniques for forming appropriate structures from the precursors for use in a fluidized bed reactor or in a fixed tube heat exchanger type reactor are well known to those skilled in the art. For example, the precursors can be structured for use in a fluidized bed reactor by depositing the phosphorus-vanadium-oxygen precursors from solution on a carrier such as titania or alumina. Alternatively, the dried precursors can be comminuted for use in a fluidized bed reactor. On the other hand, the precursors can be structured for use in a fixed tube reactor by prilling or tabletting the precursors.

In a preferred embodiment, the aqueous solution containing the phosphorus-vanadium-oxygen precursor is evaporated to apparent dryness. The dry precursor is then formed into structures by any of several well known methods, by known methods involving compression or extrusion, or by other methods known generically as "agglomeration", by which is meant the particles are simply brought together, often with a binder, to form larger particulates. Alternatively the structure may be formed by wetting the dry precursor to form a putty; then extruding the putty through a die, drying the extrudate and dividing the extrudate into pellets or tablets. Alternatively, the extrudate can be divided into pellets before drying and this latter procedure is preferred where extrusion is employed.

According to the prior art process and process improvement of the present invention, it is necessary to calcine the phosphorus-vanadium-oxygen precursors after they are formed into the structures. According to the present process improvement, calcining is at 325°-375° C., preferably 345°-360° C. in the presence of a saturated hydrocarbon, preferably butane, and air. The workable concentration of hydrocarbon in the air is 0.1-1.5 mole %. The preferred concentration of butane is about 0.8-1.2 mole %. If the concentration of hydrocarbon is lower the effect will be minimal. If the concentration is higher the reaction mixture will be at an explosive level. Within the specified limits there may be performance variations when employing different hydrocarbons or different reaction conditions. Adjustment for achieving maximum performance is desirable. Within the temperature range indicated, typical calcining terms run about 24 hours. As indicated above this step may be conducted in the maleic anhydride reactor while converting hydrocarbon to maleic anhydride.

PREPARATION OF MALEIC ANHYDRIDE

The catalysts of the present invention are useful in a variety of reactors to convert saturated hydrocarbons to maleic anhydride. Both fluidized bed reactors and fixed tube heat exchanger-type reactors are satisfactory, and details of the operation of such reactors are well known to those skilled in the art. The reaction to convert saturated hydrocarbons to maleic anhydride requires only passing the saturated hydrocarbons admixed with a free oxygen-containing gas, such as air or oxygen-enriched air, through the catalysts at elevated temperatures. The saturated hydrocarbons are passed through the catalyst at a concentration of about 1.5 to about 10 volume percent saturated hydrocarbons at a space velocity of about 100 to 4000 cc/cc/hour to provide maleic anhydride yields of greater than 50 percent at temperatures between about 325° C. and 375° C.

In the preferred embodiment the catalysts of the present invention are particularly useful in fixed tube heat exchanger-type reactors. The tubes of such reactors can vary in diameter from about ¼ inch to about 1.5 inch and the length can vary from about six inches to about 10 or more feet. It is desirable to have the surfaces of the reactors at a relatively constant temperature and some medium to conduct heat from the reactors is necessary to aid temperature control. Such media can be Woods metals, molten sulfur, mercury, molten lead and the like, or eutectic salt baths. A metal block reactor whereby the metal surrounding the tube acts as a temperature regulating body can also be used. The reactor or reaction tubes can be iron, stainless steel, carbon steel, glass and the like.

Maleic anhydride produced by using the catalysts of this invention can be recovered by any number of means well known to those skilled in the art. For example, the maleic anhydride can be recovered by direct condensation or by absorption in suitable media with subsequent separation and purification of the anhydride.

The pressure in the reactor is not generally critical; therefore, the reaction can be at atmospheric, super atmospheric or subatmospheric pressure, although superatmospheric pressure is usually employed.

A large number of saturated hydrocarbons having from 4 to 10 carbon atoms can be converted to maleic anhydride using the catalysts of the present invention. It is only necessary that the hydrocarbon contains not less than four carbon atoms in a straight chain. As an example, the preferred saturated hydrocarbon is butane. Isobutane, which does not contain four carbon atoms in a straight-chain, is not satisfactory for conversion to maleic anhydride although its presence is not harmful. In addition to butane, other saturated hydrocarbons within the scope of this invention include the pentanes, the hexanes, the heptanes, the octanes, the nonanes, the decanes or mixtures of any of these with or without butane. In addition to the above compounds, cyclic compounds such as cyclopentane or cyclohexane are satisfactory feed materials for conversion to maleic anhydride. Also, the feed stocks do not necessarily have to be totally saturated but can be technical grade hydrocarbons containing up to about 25 weight percent of olefinically unsaturated hydrocarbons, or other hydrocarbon fractions.

The principal product from the oxidation of the above feed materials is maleic anhydride. It should be noted that small amounts of citraconic anhydride may also be produced when the feed stock is a saturated hydrocarbon containing more than 4 carbon atoms.

EXAMPLES

To a mixture of 340.0 grams (1.87 moles) of vanadium pentoxide, 1150 milliliters of water, and 2.3 grams of STEROX ®NJ nonionic surfactant (nonylphenolethylene oxide condensate, manufactured by Monsanto) were added 228.0 grams (1.98 moles) of 85% orthophosphoric acid and 173.0 grams (2.06 moles) of 97.6% phosphorous acid. The phosphorus to vanadium atom ratio was about 1.08:1. The aqueous mixture of vanadium and phosphorus compounds was charged to a 2-liter Parr autoclave, fitted with a thermowell, two 6-bladed stirrers, and a vent, and heated to about 100° C. The autoclave was thereafter sealed. The mixture, while being stirred at 1,000 revolutions per minute (rpm), was heated to about 150° C. in about 50±10 minutes and held at this temperature for about 4 hours. After the hold period, the autoclave was cooled to about 80° C. in 50±10 minutes and opened. The aqueous phosphorus-vanadium-oxygen catalyst precursor slurry was placed in an open dish casserole and evaporated to dryness in an oven at 120° C. The remaining solids were ground to pass an 18 mesh sieve (U.S. Standard Sieve Size) and formed into 0.48 centimeter diameter tablets using 1 weight percent graphite as a pelletizing lubricant.

EXAMPLE 1 (comparative)

The catalyst was calcined in air using a tray furnace by heating to 400° C. in about 2 hours and holding at 400° C. for about 6 hours. The catalyst was tested by placing the tablets in a 2.1-centimeter inside diameter fixed tube reactor which was 15.2 centimeters long. At a temperature of about 400° C. using a feed stream containing 1.5 mole percent n-butane in air at a space velocity of about 1450 cc/cc/hour, the n-butane was converted to maleic anhydride. The yields of maleic anhydride shown in Table I represent performance after the catalysts had been conditioned for at least 16 hours.

EXAMPLE 2

The catalyst was calcined in situ in a maleic anhydride reactor by heating to 400° C. in 4.25 hours in an air steam. Space velocity was about 1450 cc/cc/hr. The catalyst was then held at 400° C. for 24 hours in a stream containing 1% n-butane in air at a space velocity of 1450 cc/cc/hr. Performance is shown in Table I after conditioning for at least 16 hours at 1.5%, 1450 cc/cc/hr.

EXAMPLE 3

The catalyst was calcined in situ in a maleic anhydride reactor in a feed stream containing 1% n-butane in air at 1450 cc/cc/hr. It was heated to 350° C. in about 4 hours and held at this temperature for 24 hours. Performance is shown in Table I after conditioning for at least 16 hours at 1.5%, 1450 cc/cc/hr.

TABLE I

| Example | n-Butane Feed, Mole, % | Space Velocity cc/cc/hr | Bath Temp. °C. | MAN Yield |
|---|---|---|---|---|
| 1 | 2.0 | 1463 | 410° | 50.3% |
| 1 | 2.0 | 2002 | 414° | 46.1% |
| 2 | 2.0 | 1451 | 410° | 48.2% |
| 2 | 2.0 | 2006 | 409° | 43.1% |
| 3 | 2.0 | 1465 | 407° | 54.4% |
| 3 | 2.0 | 2032 | 409° | 50.5% |

We claim:

1. In a method for the preparation of a phosphorus-vanadium-oxygen-containing complex catalyst comprising:

(a) contacting vanadium and phosphorus compounds under conditions which will provide a catalyst precursor wherein greater than 50 atom % of the vanadium is in the tetravalent state;

(b) recovering the catalyst precursor;

(c) forming the catalyst precursor into agglomerates; and (d) calcining the catalyst precursor agglomerations at a temperature between about 300° C. and 600° C.

the improvement consisting essentially of calcining in one temperature range at 325°-375° C. the catalyst precursor in the presence of a 0.1-1.5 mole percent concentration of a saturated aliphatic hydrocarbon in air.

2. The method improvement of claim 1 wherein the saturated aliphatic hydrocarbon is butane.

3. The method improvement of claim 1 wherein temperature of calcination is 345°-360° C.

4. The method improvement of claim 1 wherein temperature of calcination is about 350° C.

5. The method improvement of claim 2 wherein the concentration of butane in air is 0.8-1.2 mole percent.

* * * * *